United States Patent [19]

Doat et al.

[11] Patent Number: 4,761,400

[45] Date of Patent: Aug. 2, 1988

[54] LAXATIVE COMPOSITION BASED ON LACTULOSE AND ITS PREPARATION PROCESS

[75] Inventors: Bernard J. M. Doat; Jean-Francois J. Letavernier, both of Angers; Gilbert G. Aubard, Palaiseau; Jean B. Llull, Morsang sur Orge; Alain P. Calvet, Versailles; Jean-Louis Junien, Paris, all of France

[73] Assignee: Jouveinal S.A., Paris, France

[21] Appl. No.: 816,617

[22] Filed: Jan. 6, 1986

[30] Foreign Application Priority Data

Jan. 15, 1985 [FR] France ............................. 85 00528

[51] Int. Cl.$^4$ .................... A23L 1/236; A61K 31/70
[52] U.S. Cl. ........................................ 514/53; 426/548
[58] Field of Search ......................... 514/53; 426/548

[56] References Cited

U.S. PATENT DOCUMENTS

| | | | |
|---|---|---|---|
| 3,272,705 | 9/1966 | Petuely | 514/53 |
| 3,860,707 | 1/1975 | Wootton | 514/53 |
| 3,860,708 | 1/1975 | Prout | 514/53 |
| 3,865,957 | 2/1975 | Schieweck et al. | 426/548 |
| 4,096,285 | 6/1978 | Burge et al. | 426/548 |
| 4,122,205 | 10/1978 | Burge et al. | 426/548 |
| 4,536,221 | 8/1985 | Carobbi et al. | 536/125 |
| 4,605,646 | 8/1986 | Bernardi | 514/53 |

*Primary Examiner*—Edward A. Miller
*Attorney, Agent, or Firm*—Cushman, Darby & Cushman

[57] ABSTRACT

Lactulose-based laxative composition which is in the form of a jelly with a viscosity at 20° C. measured on the Brookfield viscosimeter between 15,000 and 30,000 centipoises, a refractive index at 20° C. between 1.430 and 1.445 and a pH between 3 and 4.

17 Claims, No Drawings

LAXATIVE COMPOSITION BASED ON LACTULOSE AND ITS PREPARATION PROCESS

The present invention relates to a novel lactulose-based composition, essentially intended for the treatment of constipation in man.

Constipation very frequently occurs and affects a large number of individuals with no distribution as regards sex or age. Its causes and consequences vary considerably. In numerous simple cases, a correction to the diet is sufficient to reestablish a normal state.

However, laxative drugs are necessary and/or indispensable in the more serious cases, such as functional constipation or in special situations, such as certain radiological examinations, the consequences of operations or confinements, as well as in the treatment of young children and elderly people.

There are numerous laxative substances and many of them have been known for a very long time. They can be of a vegetable, mineral or synthetic nature. Their use has well known unpleasant effects, which it would be advantageous to eliminate.

To this end, the relatively recent use as laxative substances of non-assimilatable water soluble saccharides, such as lactulose has led to an undoubted advance.

Lactulose or 4-O-$\beta$-D-galactopyranosyl-D-glucose, which was prepared in 1930, was proposed in about 1960, in solution form, for the treatment of constipation. Numerous toxicological, pharmacological and clinical studies guaranteed its harmlesness and effectiveness. The product has been marketed in various countries in syrup form (Duphalac in France 1972).

Lactulose is industrially manufactured by the isomerization of lactose under the influence of various alkaline agents. No matter what the said agent, the lactulose obtained is accompanied by related sugars, the most important of these being galactose and lactose.

The product obtained is in the form of a concentrated solution, which can be directly used with or without adjuvants for the preparation of syrups. However, these syrups suffer from disadvantages. Their hyperosmolarity accompanied by a very sugared and sweetish taste is sometimes the cause of repulsion and can lead to nausea. In frequent long term treatment cases, lassitude when such syrups have to be repeatedly absorbed is encountered in elderly patients. The dosage of the treatment varies on the one hand as a function of the patient involved (children - adults) and on the other hand as a function of the individual patient. Thus, the useful dose depends on the case and the individual and the measurement of an even approximate syrup quantity is subject to error, particularly in the case of the small quantities used for the treatment of young children.

In order to obviate these disadvantges, attempts have been made to dehydrate concentrated lactulose syrups into a powder. The elimination of the water by sudden heat treatment in the presence of an adjuvant has been described in German Patent No. 27 17 707. A caramelized product is obtained, in connection with which there can be doubts whether the quantity and nature of the lactulose introduced before treatment have been respected. Gentler methods have been described and in particular atomization and lyophilization.

French Patent No. 2 139 789 describes the preparation by atomization or lyophilization of a powder having a high lactulose content. In order to obtain a product which can be conveniently handled, use is made of an adjuvant, namely Konnyaku flour, which constitutes an inactive charge or filler. However, the use of this adjuvant requires previous handling operations, namely the grinding of the adjuvant, dissolving in water and filtering the solution. The thus obtained adjuvant solution is added to a concentrated lactulose syrup, so as to obtain a mixture having an appropriate viscosity for atomization or lyophilization.

The powder obtained rehumidifies in the ambient air and after one month resorbs approximately 4.5 to 8% water.

This process requires uneconomic handling operations and only leads to a moisture-sensitive product, which cannot therefore be used after a normal period of storage.

The lyophilization without adjuvant of a lactulose syrup does not give a satisfactory result (Japanese Patent No. 52-21063). The elimination of the water is incomplete and the product obtained by this method is hygroscopic, tends to rehydrate in the presence of ambient moisture and consequently gives a difficultly handleable gummy product.

French Patent No. 2 392 031 describes an improvement to this process consisting, when starting from a product obtained by lyophilization, eliminating the residual water by a treatment with non-denatured absolute ethanol, which makes it possible to obtain a non-hygroscopic, handleable lactulose powder.

As a result of the price of the absolute ethanol, this treatment affects the already high price of the product obtained by lyophilization and also requires a perfect drying of the powder to eliminate residual ethanol traces. If this stage is inadequately performed, the treated patient can absorb by no means negligible ethanol quantities.

U.S. Pat. Nos. 3,860,708 and 3,867,524 propose the administration in man of 50% by weight lactulose syrup in order to eliminate the barium sulphate retained in the intestine following the absorption of this product as an opacifier during certain radiological examinations and for treating the ailments resulting from periodontitis. These two patents identically point out that lactulose can be not only in the preferred form of a syrup, but also in other pharmaceutical forms, including jelly drops. To this end, it is proposed that pectin be used as the jellifying agent, sorbic acid and its salts as preservatives and citric and tartaric acid as organoleptic agents. Without being given further details, the pharmaceutical chemist is led to the conclusion that these jelly drops were prepared, if at all, by the action of a standard pharmaceutical pectin on lactulose syrup. In this pectin, conventionally used in pharmaceutical chemistry and called "highly esterified", more than 50% of the carboxylic groups of the polygalacturonic acid are esterified by methanol.

The Applicant has carried out jellifying tests of this type. The mixture of normal lactulose syrup, i.e. with a water soluble dry substance content below 63% by weight and conventional pectin does not make it possible to obtain a jelly. Jellifying only takes place if the content of water soluble dry substances of the lactulose is raised to a value exceeding 65% by weight. However, as is indirectly confirmed by claim 2 of U.S. Pat. No. 3,867,524, the maximum water soluble dry substance content of a normal lactulose syrup is 63%. It therefore follows that the lactulose syrup previously underwent evaporation to increase its dry substance content or, and which is more likely, jelly drops were not in fact prepared.

In order to evaporate lactulose syrup, it is necessary to raise it to a temperature exceeding 100° C. and said evaporation is necessarily accompanied by a denaturation of the lactulose.

No matter what the processes described or assumed for the preparation of a lactulose-based composition, they call on complicated technology and therefore require complicated equipment.

The invention breaks with this prior art defined by the aforementioned patents, which tended to lead to lactulose in powder or pseudo-solid form.

The present invention therefore specifically relates to a process for the preparation of a lactulose-based laxative composition, wherein it comprises:

(a) raising the aqueous lactulose syrup with a water soluble dry substance content below 63% by weight to a temperature between 20° and 90° C., (b) adding to the lactulose syrup a water soluble calcium or magnesium salt in an amount of 0.1 to 1% by weight compared with the weight of the syrup and a pharmaceutically acceptable pH-adjusting agent in a quantity such that the pH of the syrup to which the salt and adjusting agent have been added is between 2.5 and 5, whereby stage (b) can be performed before, during or after stage (a), then (c) adding to the syrup, raised to between 20° and 90° C. and to which the salt and pH-adjusting agent have been added, 0.1 to 5% by weight with respect to the syrup weight of a pectin having a percentage of esterified carboxylic groups below 50, then, (d) stirring the syrup and pectin for at least 5 minutes and then, (e) leaving the syrup and pectin to cool to a temperature where jellification takes place.

This leads to a lactulose-based composition in the form of a jelly with a viscosity of 20° C. on the Brookfield viscosimeter between 15,000 and 30,000 centipoises and a refractive index at 20° C. between 1.430 and 1.445, with a pH between 3 and 4.

Thus, the lactulose composition is not prepared in solid form, but in so doing and instead obtaining a viscous jellified state similar to a jam, which cuts easily, not only as is possible to essentially obtain all the requisite properties, particularly stability and shaping of doses, but it is also possible to use the product in masked form. Thus, compromising on the solid state makes it possible to achieve these advantages without any disadvantage, whereas the prior art was so keen at maintaining the solid state.

The first stage of the process according to the invention for the preparation of a lactulose-based laxative composition consists of raising the lactulose syrup with a water soluble dry substance content below 63% by weight to between 20° and 90° C.

The concentrated lactulose syrups have a water soluble dry substance content which is normally between 50 and 63% by weight of water soluble dry substances. They are present in the form of pale yellow, clear syrups with a density close to 1.310. In general, the lactulose represents 45 to 55% by weight of the syrup. It is accompanied by other related substances, such as lactose, epilactose, galactose, levulose and tagatose, which normally represent 5 to 12% by weight of the syrup.

The syrup is heated to a temperature between 50° and 75° C., in order to adequately fluidize the syrup, but without approaching excessively the denaturation temperature.

The second stage of the process according to the invention consists of adding to the lactulose syrup a water soluble calcium or magnesium salt, at a rate of 0.1 to 1% by weight compared with the syrup weight. Particular preference is given to calcium salts and in particular calcium chloride and calcium lactate.

To the syrup is also added a pharmaceutically acceptable pH-adjusting agent in a quantity such that the pH of the syrup to which the salt and adjusting agent have been added is between 2.5 and 5 and preferably between 3 and 4. The pH-adjusting agent is preferably constituted by an organic acid and more specifically citric or tartaric acid, as a result of their organoleptic properties. For example 0.1 to 1% by weight of pH-adjusting agent is added per 100 parts by weight of syrup.

It is possible to reverse the first and second stages of the process according to the invention or perform them simultaneously.

The third stage of the process according to the invention consists of adding to the syrup, heated to between 20° and 90° C. and to which the salt and pH-adjusting agent have been added, 0.1 to 5% by weight, based on the syrup weight, of a pectin having below 50% of esterified carboxylic groups.

Pectins are carbohydrates generally obtained from dilute acid extracts of lemon or apple pulp. They are also present in the cellular walls of vegetables and fruits. They are also contained in root crops such as carrots and beetroot, as well as in tubers, such as potatoes. Pectins are chemically defined as partial methyl esters of polygalacturonic acids, whereof the molecular weight can reach 200,000.

Among these pectins, the invention does not call on the highly esterified pectins conventionally used in the pharmaceutical industry and instead uses slightly esterified pectins particularly obtained by partial hydrolysis of the ester functions of pectins highly esterified under the action of ammonia. They are characterized by an esterification percentage of the carboxylic functions below 50% and preferably between 18 and 39%. The esterification percentage is determined according to the method defined in the U.S.P., XXI-NF XVI 1985, p 790. The slightly esterified pectins have amide functions. Their amidification index is generally between 12 and 25%. This index represents the carboxylic function percentage converted into amide function during treatment by ammonia. A process for determining this index is given in FAO Food and Nutrition Paper (specifications for identity and purity of carrier solvents, emulsifiers, stabilizers, enzyme preparations, flavoring agents, food colors, sweetening agents and other food additives), Geneva, 23.3. to 1.4.1981.

The fourth stage of the process according to the invention consists of stirring the syrup and pectin for at least 5 minutes and generally for between 15 minutes and 2 hours to obtain a good homogeneity.

The final stage of the process according to the invention consists of leaving the syrup and pectin to cool to a temperature where jellification occurs and particularly to ambient temperature of 15° to 25° C. However, a lower temperature or even a slightly higher temperature may be suitable.

This leads to a laxative composition which preferably has a viscosity between 18,000 and 25,000 centiposes and a refractive index between 1.35 and 1.440. This lactulose-based composition conventionally contains 35 to 45% by weight lactulose, 40 to 55% by weight water and an adequate quantity of a pectinocalcium system to give the composition the texture of a jelly having the aforementioned viscosity, refractive index and pH values.

Preferably, the composition incorporates an adequate flavoring agent quantity to mask the taste of the lactulose. The flavoring agents are chosen in order to identify to the best possible extent the jellies with natural products, both from the standpoint of appearance and from the standpoints of odor and flavor. Most commonly use is made of the following flavors: black currant, red currant, raspberry, prune, quince, orange, lemon, mandarin, fig, etc.

The addition of an antifungal product makes it possible to ensure that the jelly keeps well. To this end preference is given to the use of sorbic acid and more particularly potassium sorbate in quantities representing 0.01 to 0.5% by weight based on the weight of the composition.

The following examples illustrate the invention.

EXAMPLE 1

In order to illustrate the preparation of a preferred composition according to the invention, a description is given hereinafter of the preparation of a 200 kg batch, whose composition for 100 grams is as follows:

| | |
|---|---|
| 50% lactulose syrup (58% water soluble dry substances) | 80.992 g |
| citric acid | 0.350 g |
| calcium lactate | 0.108 g |
| slightly esterified pectin of type A (with an esterification percentage of 33%, an amidation percentage of 16% and a pH of the 1% solution of 4.7) | 0.700 g |
| water soluble prune-type natural flavor | 1.000 g |
| potassium sorbate | 0.050 g |
| purified water | 16.800 g |

A solution is prepared by dispersing 1.40 kg of pectin in 33.60 kg of water previously heated to 70° C. After stirring for 15 to 20 minutes, a homogeneous solution is obtained.

In parallel, 162 kg of 50% lactulose syrup is introduced into a "turbosphere". This syrup is heated, accompanied by stirring, to 70° C., followed by the successive introduction, whilst dispersing, of 216 g of calcium lactate and then 100 g of potassium sorbate.

Following the dissolving of these products in the syrup at 70° C., there is a gradual introduction of 700 g of citric acid, whilst allowing dissolving to take place between each addition. Following this addition, the pH of the mixture is approximately 3.5. This is followed by the introduction in approximately 10 minutes of the previously prepared pectin solution. Stirring is maintained for 10 minutes followed by the introduction of 2 kg of prune flavor into the mixture. Cooling to 25° C. takes place and the jelly obtained is placed into 8 to 50 g unit doses.

On the Brookfield viscosimeter, the jelly has a viscosity of 22,000 centipoises and a refractive index of 1.438, both at 20° C. This jelly has an appearance and texture like that of a food jelly. It can be easily and cleanly cut with a spoon and does not adhere to the walls of glass or plastic containers. Its easy handling is made possible by its stiffness. The jelly is not runny, but is sufficiently flexible to have a pleasing taste for the palate. The appearance and organoleptic properties of the jelly are not impaired by storing for 18 months at ambient temperature. The jelly retains its translucent appearance and texture up to a temperature of approximately 35° C. It tends to liquify at above 40° C., but then reassumes its initial physical state by cooling.

EXAMPLE 2

Example 1 is repeated, but with the following formulation:

| | |
|---|---|
| 50% lactulose syrup (58% of water soluble dry substances) | 81.40 g |
| citric acid | 0.25 g |
| dehydrated calcium chloride | 0.05 g |
| type B pectin with a 31% esterification percentage, a 17% amidation percentage and a pH of the 1% solution of 4.9 | 0.70 g |
| prune-type soluble flavor | 0.80 g |
| potassium sorbate | 0.50 g |
| water | 16.30 g |

A product is obtained having an appearance and physical properties like those of example 1.

EXAMPLE 3

Example 2 is repeated, except that the pectin is of type C having an esterification percentage of 21%, an amidation percentage of 23% and a pH of the 1% aqueous solution of 4.6.

The composition has an appearance and organoleptic properties similar to those of example 2. The jelly tends to liquify as from 30° C., but reassumes its initial appearance by cooling to 15° to 20° C.

EXMAPLE 4

Example 1 is repeated, but with the following formulation for 100 grams:

| | |
|---|---|
| 50% lactulose syrup | 81.00 g |
| citric acid | 0.35 g |
| potassium sorbate | 0.05 g |
| xanthan gum | 1.00 g |
| prune flavor | 1.00 g |
| water | 16.60 g |

The composition obtained has a gummy pseudo-jellified texture. Gripping is difficult, the product sticks to the spoon, to glass and to plastics in much the same way as honey.

EXAMPLE 5

(comparative)

Example 4 is repeated, but the xanthan gum is replaced by 2 g of carob gum. The composition obtained is not a jelly. It has a viscous, sticky texture and is very difficult to grip, whilst giving off an unpleasant smell.

EXAMPLE 6

(comparative)

Example 5 is repeated, except that the carob gum is replaced by 1 g of "250 Bloom" gelatin. USP XXI NF XVI, 1985, p 1329 defines the degree bloom, which characterizes the jellification force of gelatin.

The composition obtained has an excessively hard consistency to be easily removed with a spoon. A brown coloring appears and increases over a period of time. The composition is made unusable as a result of this brown coloring alone, which is due to the Maillard reaction between the protein amino functions of the gelatin and the hydroxyl functions of the lactulose.

EXAMPLE 7

(comparative)

Example 4 is repeated, except that the xanthan gum is replaced by 1.20 g of a pectin having a 65% esterification percentage. The composition of the lactulose obtained is not that of a jelly and instead has a very syrupy consistency. It sticks to the spoon, as well as to glass and plastic walls.

EXAMPLE 8

(comparative)

Example 7 is repeated, whilst adding 0.80 g of calcium lactate. The composition obtained has an appearance, a consistency and properties similar to those of example 7.

The conditioning of the jellies according to the invention can take place in conventional containers of the type used for jam. These lactulose-based jellies are particularly suitable for presentation in the form of unit doses, which are not very practical for the syrup form and uncertain for the powder form, due to the potential hydroscopicity thereof.

Presentation in the form of unit doses has the following advantages:
ensuring the absorbed dose,
contamination of multiple samples avoided,
unused doses preserved during a treatment stoppage,
ease and reliability of use due to the texture of the jelly form,
possibility of use in masked form, e.g. on bread and jam, in yoghurt, etc.,
facility of dividing up doses, particularly for treating young children,
reduction of the monotony during prolonged treatment by varying the flavors and odors of the jellies, etc.,
better preservation of the product, particularly with respect to oxidation phenomena, which lead to denaturing of the flavors and coloring of the products.

The conditioning into unit doses can easily be carried out in single dose containers obtained by thermoforming plastics materials of appropriate qualities.

The jelly can be distributed in unit doses between 8 and 50 g. The unit doess of 8 g corresponding to approximately 3.5 g of lactulose (40%) are particularly indicated in the treatment of constipation in young children, doses of approximately 25 g for the maintenance treatment in adults and doses of 50 g for initial treatment or in the case of severe constipation.

The daily dosage is 1.75 to 60 g of lactulose, as a function of the age of the patient and the severity of the constipation to be treated. These doses can be easily measured, on the basis of the aforementioned unit doses.

The lactulose-based composition according to the invention is a novel, attractively presented product, which is useful in treating constipation in most cases and particularly in children, elderly patients, as well as following confinements or operations and in particular after hemorrhoidectomies, pre-radiological or post-radiological interventions, as well as in certain medicinally caused constipation cases.

We claim:

1. A process for the preparation of a lactulose-based laxative composition comprising
   (a) heating an aqueous lactulose syrup having a dry, water soluble substance content below 63 weight percent to a temperature ranging from 50° to 90° C.,
   (b) adding to said lactulose syrup, before, during or after step (a), a water soluble calcium or magnesium salt in an amount ranging from 0.1 to 1 weight percent based on the weight of said syrup and adjusting the pH of the resulting mixture to a pH ranging from 2.5 to 5 with a pharmaceutically acceptable pH-adjusting agent,
   (c) adding to the heated and pH-adjusted water soluble calcium or magnesium salt containing syrup of step (b) a pectin having less than 50 percent of its carboxylic functions esterified in an amount ranging from 0.1 to 5 weight percent based on the weight of said syrup,
   (d) stirring the pectin containing syrup of step (c) for at least 5 minutes, and
   (e) cooling said pectin containing syrup of step (d) to a temperature sufficient to gel the same.

2. The process of claim 1 wherein said aqueous lactulose syrup is heated in step (a) to a temperature ranging from 50° to 75° C.

3. The process of claim 1 wherein said aqueous lactulose syrup in step (a) has a dry, water soluble substance content ranging from 50 to 63 weight percent.

4. The process of claim 1 wherein said water soluble calcium or magnesium salt is calcium chloride, calcium lactate, magnesium chloride or magnesium lactate.

5. The process of claim 1 wherein said pharmaceutically acceptable pH-adjusting agent is citric acid or tartaric acid.

6. The process of claim 1 where in step (b) the pH is adjusted to a pH ranging from 3 to 4.

7. The process of claim 1 wherein said pectin has from 18 to 39 percent of its carboxylic functions esterified.

8. The process of claim 7 wherein said pectin has a degree of amidification ranging from 12 to 25 percent.

9. The process of claim 1 wherein the pectin containing syrup in step (d) is stirred for a time ranging from 15 minutes to 2 hours.

10. The process of claim 1 wherein the pectin containing syrup is cooled in step (e) to a temperature ranging from 15° to 25° C.

11. A lactulose-based laxative composition prepared in accordance with the process of claim 1, said composition being in the form of a jelly having a viscosity at 20° C., as measured on a Brookfield viscometer, between 15,000 and 30,000 centipoises, a refractive index at 20° C. between 1.430 and 1.445 and a pH between 3 and 4.

12. The composition of claim 11 having a viscosity between 18,000 and 25,000 centipoises and a refractive index between 1.435 and 1.440.

13. The composition of claim 11 which also includes a flavoring agent in an amount effective to mask the taste of lactulose.

14. The composition of claim 11 in the form of 8 to 50 gram unit doses, each containing 35 to 45 weight percent lactulose.

15. A lactulose-based laxative composition comprising (a) 35 to 45 weight percent lactulose, (b) 40 to 55 weight percent water, (c) a pectinocalcium system in an amount effective to impart to said composition a texture of jelly whereby said composition has a viscosity, measured on a Brookfield viscosimeter, at 20° C., between 15,000 and 30,000 centipoises, and a refractive index at 20° C. between 1.430 and 1.445 and (d) a pH-adjusting agent in an amount effective to impart to the composition a pH ranging from 3 to 4.

16. The composition of claim 15 which also includes a flavoring agent in an amount effective to mask the taste of lactulose.

17. The composition of claim 15 in the form of 8 to 50 gram unit doses, each containing from 35 to 45 weight percent lactulose.

* * * * *